United States Patent [19]

Phillips et al.

[11] Patent Number: 4,943,381
[45] Date of Patent: Jul. 24, 1990

[54] NITROGEN-CONTAINING ADDITIVES FOR NON-AQUEOUS FUNCTIONAL FLUIDS

[75] Inventors: Emyr Phillips, Sale; Robert M. Neil, Boothstown, both of England; Hermann O. Wirth, Bensheim, Fed. Rep. of Germany

[73] Assignee: Ciba-Geigy Corporation, Ardsley, N.Y.

[21] Appl. No.: 366,118

[22] Filed: Jun. 14, 1989

Related U.S. Application Data

[62] Division of Ser. No. 195,553, May 18, 1988, Pat. No. 4,859,354, which is a division of Ser. No. 838,986, Mar. 12, 1986, Pat. No. 4,762,628.

[51] Int. Cl.$^5$ .......................................... C10M 129/04
[52] U.S. Cl. .................. 252/51.5 R; 252/77; 252/392
[58] Field of Search .................. 252/51.5 R, 77, 392

[56] References Cited

U.S. PATENT DOCUMENTS

| | | | |
|---|---|---|---|
| 4,549,882 | 10/1985 | Knapp | 44/53 |
| 4,551,257 | 11/1985 | Horodysky | 252/51.5 A |
| 4,732,691 | 3/1988 | Wirth et al. | 252/51.5 A |
| 4,830,770 | 5/1989 | Wirth et al. | 252/51.5 A |

OTHER PUBLICATIONS

Chem. Abst., 92, 169055g (1980).
Chem. Abst. 93, 53779n (1980).

*Primary Examiner*—Jacqueline V. Howard
*Attorney, Agent, or Firm*—Harry Falber

[57] ABSTRACT

The invention relates to non-aqueous functional fluids which contain at least one compound of formula I

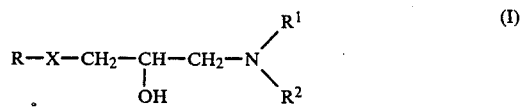

wherein X is —O—, —S—, —SO—, —SO$_2$—, —C(O)—O— or —N(R$^3$)—, in which R$^3$ is hydrogen or C$_1$–C$_{12}$alkyl, R$^1$ is unsubstituted C$_1$–C$_4$alkyl or C$_2$–C$_5$alkyl substituted by one to three hydroxyl groups, R$^2$ is hydrogen, unsubstituted C$_1$–C$_4$alkyl or C$_2$–C$_5$alkyl substituted by one to three hydroxyl groups, with the proviso that at least one of the residues R$^1$ or R$^2$ is hydroxy-substituted, and wherein R is C$_2$–C$_{20}$-alkyl, a residue —CH$_2$—CH(OH)—CH$_2$—NR$^1$R$^2$, in which R$^1$ and R$^2$ have their previous significance, or R is C$_2$–C$_{18}$alkenyl, C$_2$–C$_3$alkynyl or C$_5$–C$_{12}$cycloalkyl, with the proviso that, when X is —O— or —C(O)—O—, R is branched C$_4$–C$_{20}$alkyl, especially a tertiary alkyl group.

The compounds of formula I are very suitable as corrosion inhibitors for non-aqueous functional fluids.

8 Claims, No Drawings

NITROGEN-CONTAINING ADDITIVES FOR NON-AQUEOUS FUNCTIONAL FLUIDS

This is a divisional of application Ser. No. 195,553 filed on May 18, 1988, now U.S. Pat. No. 4,859,354 which is a divisional of Ser. No. 838,986 filed on Mar. 12, 1986, now U.S. Pat. No. 4,762,628.

The present invention relates to non-aqueous functional fluids which contain nitrogen-containing compounds, to novel nitrogen-containing compounds and to a process for the preparation of said nitrogen-containing compounds.

In U.S. Pat. No. 2 856 363 there are described compounds of the formula RCH(OH)CH(R')N(Y)R"OH, in which R is $C_2$-$C_{12}$alkyl, R' is hydrogen or $C_2$-$C_{12}$alkyl, R" is a $C_2$-$C_5$hydrocarbon chain and Y is hydrogen or R"—OH. Specifically disclosed compounds are those of formulae $C_{10}H_{23}$—CH(OH)—$CH_2$—NH—$CH_2$—$CH_2$—OH and $C_{10}H_{23}$—CH(OH)—$CH_2$—N($CH_2$—$CH_2$—OH)$_2$. The compounds are described as corrosion inhibitors in lubricating oils.

Further, in GB Patent Specification 1 152 947 there are described N-(2-hydroxy-3-alkoxypropyl)ethanolamines and N-(2-hydroxy-3-alkoxypropyl)diethanolamines and quaternary ammonium salts thereof as antistatic agents for polymers. In GB Patent Specification 979 667 there are described adducts of mono- or dialkanolamines with glycidyl alkyl esters as starting materials in the preparation of polyurethanes.

Furthermore, in GB Patent Specification 980 003 there are described 1-N-alkyl- and 1-N-hydroxyalkyl-3-alkylcarboxy-2-propanols and the quaternary ammonium salts thereof for use in cosmetic preparations.

The present invention relates to compositions which contain a non-aqueous functional fluid and at least one compound of formula I

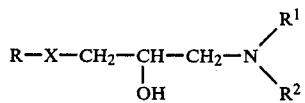
(I)

wherein X is —O—, —S—, —SO—, —$SO_2$—, —C(O)—O— or —N($R^3$)—, in which $R^3$ is hydrogen or $C_1$-$C_{12}$alkyl, $R^1$ is unsubstituted $C_1$-$C_4$alkyl or $C_2$-$C_5$alkyl substituted by one to three hydroxyl groups, $R^2$ is hydrogen, unsubstituted $C_1$-$C_4$alkyl or $C_2$-$C_5$alkyl substituted by one to three hydroxyl groups, with the proviso that at least one of the residues $R^1$ or $R^2$ is hydroxy-substituted, and wherein R is $C_2$-$C_{20}$alkyl, a residue —$CH_2$—CH(OH)—$CH_2$—$NR^1R^2$, in which $R^1$ and $R^2$ have their previous significance, or R is $C_2$-$C_{18}$alkenyl, $C_2$-$C_3$alkynyl or $C_5$-$C_{12}$cycloalkyl, with the proviso that, when X is —O— or —C(O)—O—, R is branched $C_4$-$C_{20}$alkyl, especially a tertiary alkyl group.

R as $C_2$-$C_{20}$alkyl may be straight chain or branched alkyl, e.g. ethyl, n-propyl, isopropyl, n-butyl, isobutyl, sec-butyl, tertbutyl, pentyl, hexyl, heptyl, octyl, nonyl, decyl, undecyl, dodecyl, tridecyl, tetradecyl, pentadecyl, hexadecyl, heptadecyl, octadecyl or eicosyl, with $C_4$-$C_{20}$alkyl being preferred, $C_8$-$C_{20}$alkyl being particularly preferred and $C_9$-$C_{12}$alkyl being most preferred. R is preferably branched, especially tertiary, alkyl.

R as $C_2$-$C_{18}$alkenyl may be straight chain or branched alkenyl, e.g. vinyl, n-propenyl, isopropenyl, n-butenyl, isobutenyl, n-pentenyl, n-hexenyl, n-heptenyl, n-octenyl, n-nonenyl, n-decenyl, n-dodecenyl, n-tetradecenyl, n-hexadecenyl or n-octadecenyl, with $C_2$-$C_4$alkenyl being preferred.

$C_2$-$C_3$Alkynyl groups are ethynyl or propargyl groups.

$C_5$-$C_{12}$Cycloalkyl groups are exemplified by cyclopentyl, cycohexyl, cyclooctyl, cyclodecyl and cyclododecyl groups.

Unsubstituted $C_1$-$C_{12}$alkyl groups $R^3$ may be straight chain or branched, e.g. methyl, ethyl, n-propyl, n-butyl, n-hexyl, n-octyl, n-decyl, n-dodecyl, isopropyl, t-butyl or t-octyl.

Hydroxy-substituted $C_2$-$C_5$alkyl groups $R^1$ and $R^2$ are e.g. —$CH_2$—$CH_2$—OH, —$CH_2$—$CH_2$—$CH_2$—OH, —$CH_2$—CH(OH)—$CH_3$, —CH($CH_2OH)_2C_2H_5$ or —C($CH_2OH)_3$, with —$CH_2$—$CH_2$—OH being preferred.

Examples of compounds of formula I are listed in the following Table 1.

TABLE 1

$$R-X-CH_2-CH(OH)-CH_2-N\begin{matrix}R^1\\R^2\end{matrix} \quad (I)$$

| R | X | $R^1$ | $R^2$ |
|---|---|---|---|
| i-$C_9H_{19}$ | —O— | $CH_2CH_2OH$ | H |
| i-$C_9H_{19}$ | —O— | $CH_2CH_2OH$ | $CH_2CH_2OH$ |
| i-$C_9H_{19}$ | —O— | $CH_2CH(OH)CH_2OH$ | $CH_2CH(OH)CH_2OH$ |
| i-$C_{12}H_{25}$ | —O— | $CH_2CH_2CH_2OH$ | $CH_2CH_2OH$ |
| i-$C_{12}H_{25}$ | —O— | $CH_2CH_2OH$ | $CH_2CH(OH)CH_3$ |
| t-$C_9H_{19}$ | —S— | $CH_2CH_2OH$ | $CH_2CH_2OH$ |
| t-$C_9H_{19}$ | —S— | $CH_2CH(OH)CH_2OH$ | $CH_2CH(OH)CH_2OH$ |
| t-$C_{12}H_{25}$ | —S— | $CH_2CH_2OH$ | $CH_2CH_2OH$ |
| t-$C_{12}H_{25}$ | —S— | $CH_2CH_2OH$ | $CH_2CH(OH)CH_3$ |
| t-$C_{16}H_{33}$ | —S— | $CH_2CH_2OH$ | $CH_2CH_2OH$ |
| t-$C_{16}H_{33}$ | —S— | $C(CH_2OH)_3$ | H |
| t-$C_9H_{19}$ | —CO—O— | $CH_2CH_2OH$ | $CH_2CH_2OH$ |
| t-$C_{12}H_{25}$ | —CO—O— | $CH_2CH_2OH$ | $CH_2CH_2OH$ |
| n-$C_{18}H_{37}$ | —CO—O— | $CH_2CH_2OH$ | $CH_2CH_2OH$ |
| n-$C_{20}H_{41}$ | —CO—O— | $CH_2CH_2OH$ | $CH_2CH_2OH$ |
| $C_4H_9CH(C_2H_5)CH_2$ | —SO— | $CH_2CH_2OH$ | $CH_2CH_2OH$ |
| $C_4H_9CH(C_2H_5)CH_2$ | —$SO_2$— | $CH_2CH_2OH$ | $CH_2CH_2OH$ |
| n-$C_8H_{17}$ | —N($CH_3$)— | $CH_2CH_2OH$ | $CH_2CH_2OH$ |
| i-$C_8H_{17}$ | —N($CH_3$)— | $CH_2CH_2OH$ | H |

TABLE 1-continued

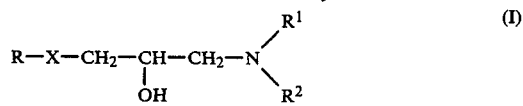

| R | X | R¹ | R² |
| --- | --- | --- | --- |
| t-$C_9H_{19}$ | —N($CH_3$)— | $CH_2CH(OH)CH_2OH$ | $CH_2CH(OH)CH_2OH$ |

Preferred compositions are those which contain a non-aqueous functional fluid and at least one compound of formula I, wherein X is —O—, —S— or —C(O)—O—, as well as those which contain at least one compound of formula I, wherein $R^1$ and $R^2$ are hydroxy-substituted $C_2$–$C_5$alkyl, especially $C_2$–$C_4$alkyl monosubstituted by hydroxy. R is preferably $C_8$–$C_{20}$alkyl, in particular branched $C_8$–$C_{20}$alkyl, most preferably tertiary $C_9$–$C_{12}$alkyl.

A further embodiment comprises compositions which contain a nonaqueous functional fluid and at least one compound of formula I, wherein X is —S—, $R^1$ is hydroxy-substituted $C_4$–$C_5$alkyl, especially $C_4$–$C_5$alkyl polysubstituted by hydroxy, and $R^2$ is hydrogen and R is $C_2$–$C_{20}$alkyl, preferably branched $C_8$–$C_{20}$alkyl, most preferably tertiary $C_9$–$C_{18}$alkyl.

Some of the compounds of formula I are known and some of the compounds of formula I are novel.

Accordingly, the invention further relates to compounds of formula I

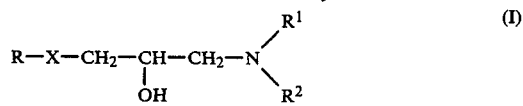

wherein X is —O—, —S—, —SO—, —SO₂—, —C(O)—O— or —N($R^3$)—, in which $R^3$ is hydrogen or $C_1$–$C_{12}$alkyl, $R^1$ is unsubstituted $C_1$–$C_4$alkyl or $C_2$–$C_5$alkyl substituted by one to three hydroxyl groups, $R^2$ is hydrogen, unsubstituted $C_1$–$C_4$alkyl or $C_2$–$C_5$alkyl substituted by one to three hydroxyl groups, with the proviso that at least one of the residues $R^1$ or $R^2$ is hydroxy-substituted, and wherein R is $C_4$–$C_{20}$alkyl, a residue —$CH_2$—CH(OH)—$CH_2$—$NR^1R^2$, in which $R^1$ and $R^2$ have their previous significance, or R is $C_2$–$C_{18}$alkenyl, $C_2$–$C_3$alkynyl or $C_5$–$C_{12}$cycloalkyl, with the proviso that, when X is —O—, —S— or —N($R^3$)—, R is branched $C_8$–$C_{20}$alkyl and, when X is C(O)—O—, R is different from $C_4$–$C_{20}$alkyl.

Preferred compounds of formula I are those wherein X is —O—, —S— or —C(O)—O—, and/or $R^1$ and $R^2$ are $C_2$–$C_5$alkyl monosubstituted by hydroxy.

Especially preferred compounds of formula I are those wherein X is —S— and/or R is preferably tertiary $C_9$–$C_{18}$alkyl.

Further preferred compounds of formula I are those wherein X is —S—, $R^1$ is hydroxy-substituted $C_4$–$C_5$alkyl, especially $C_4$–$C_5$alkyl polysubstituted by hydroxy, and $R^2$ is hydrogen and R is $C_4$–$C_{20}$alkyl, preferably $C_8$–$C_{20}$alkyl, in particular branched $C_8$–$C_{20}$alkyl, most preferably tertiary $C_9$–$C_{18}$alkyl.

A further object of the present invention is a process for the preparation of compounds of formula I by reacting a compound of formula II

R—XH     (II)

wherein X is —O—, —S—, —SO—, SO₂, —C(O)—O— or —N($R^3$)—, in which $R^3$ is hydrogen or $C_1$–$C_{12}$alkyl, and wherein R is $C_4$–$C_{20}$alkyl, a residue —$CH_2$—CH(OH)—$CH_2$—$NR^1R^2$, in which $R^1$ is unsubstituted $C_1$–$C_4$alkyl or $C_2$–$C_5$alkyl substituted by one to three hydroxyl groups, and $R^2$ is hydrogen, unsubstituted $C_1$–$C_4$alkyl or $C_2$–$C_5$alkyl substituted by one to three hydroxyl groups, with the proviso that at least one of the residues $R^1$ or $R^2$ is hydroxy-substituted, or R is $C_2$–$C_{18}$alkenyl, $C_2$–$C_3$alkynyl or $C_5$–$C_{12}$cycloalkyl, with the proviso that, when X is —O—, —S— or —N($R^3$)—, R is branched $C_8$–$C_{20}$alkyl and, when X is —C(O)—O—, R is different from $C_4$–$C_{20}$alkyl, or of a metal salt thereof, e.g. the sodium or potassium salt, in the absence or presence of a catalyst, with a compound of formula III

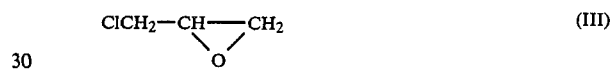

to produce a compound of formula IV

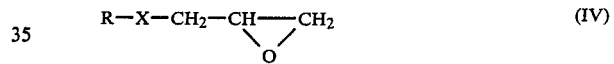

which is then reacted with an amine of formula V

wherein $R^1$ and $R^2$ have their previous significance.

The catalyst may be for example an acid, a base or a phase transfer catalyst.

The known compounds are prepared in analogous manner.

The compounds of formula I are very suitable for improving the properties, especially the corrosion-inhibiting properties in non-aqueous functional fluids.

The compounds of formula I are employed as corrosion inhibitors in non-aqueous functional fluids in amounts of 0.001 to 5% by weight, especially 0.05 to 3% by weight, based on the non-aqueous functional fluid.

The non-aqueous functional fluid may be a lubricating oil e.g. a natural or synthetic lubricating oil; a refined petroleum product such as a fuel oil, diesel oil, kerosene, gasoline or aviation fuel; or a hydraulic fluid, e.g. a phosphate-based synthetic oil.

The lubricating oil may be a mineral oil, a synthetic oil or any mixture of such oils. Mineral oils are preferred and examples of these include paraffin oils, e.g. a mineral oil having a viscosity of 46 mm²/s at 40° C.; "150 Solvent Neutral", a solvent refined neutral mineral oil having a viscosity of 32 mm²/s at 40° C.; and "Solvent brightstocks", a high-boiling residue from the process of refining mineral oil, and having a viscosity of 46 mm²/s at 40° C.

Synthetic lubricating oils which may be present are for example synthetic hydrocarbons such as polybutenes, alkyl benzenes and poly-alpha olefins as well as simple di-, tri- and tetraesters, complex esters and polyesters. Diesters are derived e.g. from carboxylic acid esters of the formula

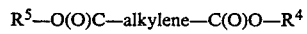

$$R^5-O(O)C-\text{alkylene}-C(O)O-R^4$$

wherein "alkylene" is a $C_2$-$C_{14}$ alkylene residue and $R^4$ and $R^5$ are the same or different and each is a $C_6$-$C_{18}$ alkyl group.

Triesters which may be used as lubricating oil basestocks are those derived from trimethylolpropane and $C_6$-$C_{18}$ monocarboxylic acids or mixtures thereof, whereas suitable tetraesters include e.g. those derived from pentaerythritol and a $C_6$-$C_{18}$ monocarboxylic acid or mixtures thereof.

Complex esters suitable for use as components of the compositions of the present invention are e.g. those derived from monobasic acids, dibasic acids and polyhydric alcohols, for instance the complex ester derived from trimethylolpropane, caprylic acid and sebacic acid.

Suitable polyesters are e.g. those derived from a $C_4$-$C_{14}$ dicarboxylic acid and at least one aliphatic dihydric $C_3$-$C_{12}$ alcohol, e.g. those derived from azelaic acid or sebacic acid and 2,2,4-trimethylhexane-1,6-diol.

The lubricating oils can also contain other additives which may be added to improve the basic properties of lubricants, e.g. antioxidants, metal passivators, rust inhibitors, viscosity-index improvers, pour-point depressants, dispersing agents, emulsifiers, extreme pressure additives and anti-wear additives. Examples of such additives are indicated below.

EXAMPLES OF PHENOLIC ANTIOXIDANTS

1. Alkylated monophenols 2,6-di-tert-butyl-4-methylphenol
2,6-di-tert-butylphenol
2-tert-butyl-4,6-dimethylphenol
2,6-di-tert-butyl-4-ethylphenol
2,6-di-tert-butyl-4-ethylphenol
2,6-di-tert-butyl-4-n-butylphenol
2,6-di-tert-butyl-4-isobutylphenol
2,6-dicyclopentyl-4-methylphenol
2-(α-methylcyclohexyl)-4,6-dimethylphenol
2,6-dioctadecyl-4-methylphenol
2,4,6-tricyclohexylphenol
2,6-di-tert-butyl-4-methoxymethylphenol
o-tert-butylphenol

2. Alkylated hydroquinones 2,6-di-tert-butyl-4-methoxyphenol
2,5-di-tert-butylhydroquinone
2,5-di-tert-amylhydroquinone
2,6-diphenyl-4-octadecyloxyphenol

3. Hydroxylated thiodiphenyl ethers 2,2'-thiobis(6-tert-butyl-4-methylphenol)
2,2'-thiobis(4-octylphenol)
4,4'-thiobis(6-tert-butyl-3-methylphenol)
4,4'-thiobis(6-tert-butyl-2-methylphenol)

4. Alkylidenebisphenols 2,2'-methylenebis(6-tert-butyl-4-methylphenol)
2,2'-methylenebis(6-tert-butyl-4-ethylphenol)
2,2'-methylenebis[4-methyl-6-(α-methylcyclohexyl)-phenol]
2,2'-methylenebis(4-methyl-6-cyclohexylphenol)
2,2'-methylenebis(6-nonyl-4-methylphenol)
2,2'-methylenebis(4,6-di-tert-butylphenol)
2,2'-ethylidenebis(4,6-di-tert-butylphenol)
2,2'-ethylidenebis(6-tert-butyl-4-isobutylphenol)
2,2'-methylenebis[6-(α-methylbenzyl)-4-nonylphenol]
2,2'-methylenebis[6-(α,α-dimethylbenzyl)-4-nonylphenol]
4,4'-methylenebis(2,6-di-tert-butylphenol)
4,4'-methylenebis(6-tert-butyl-2-methylphenol)
1,1-bis(5-tert-butyl-4-hydroxy-2-methylphenyl)butane
2,6-di(3-tert-butyl-5-methyl-2-hydroxybenzyl)-4-methylphenol
1,1,3-tris(5-tert-butyl-4-hydroxy-2-methylphenyl)-3-n-dodecylmercaptobutane
ethylene glycol bis[3,3-bis(3'-tert-butyl-4'-hydroxyphenyl)butyrate]
di(3-tert-butyl-4-hydroxy-5-methylphenyl)dicyclopentadiene
di[2-(3'-tert-butyl-2'-hydroxy-5'-methylbenzyl)-6-tert-butyl-4-methylphenyl]terephthalate.

5. Benzyl compounds 1,3,5-tri(3,5-di-tert-butyl-4-hyroxybenzyl)-2,4,6-trimethylbenzene
di(3,5-di-tert-butyl-4-hydroxybenzyl)sulfide
3,5-di-tert-butyl-4-hydroxybenzylmercaptoacetic acid isooctyl ester
bis(4-tert-butyl-3-hydroxy-2,6-dimethylbenzyl)dithiolterephthalate
1,3,5-tris(3,5-di-tert-butyl-4-hydroxybenzyl)isocyanurate
1,3,5-tris(4-tert-butyl-3-hydroxy-2,6-dimethylbenzyl)isocyanurate
3,5-di-tert-butyl-4-hydroxybenzylphosphonic acid dioctadecyl ester
3,5-di-tert-butyl-4-hydroxybenzylphosphonic acid monoethyl ester calcium salt.

6. Acylaminophenols 4-hydroxylauric acid anilide
4-hydroxystearic adid anilide
2,4-bis-octylmercapto-6-(3,5-di-tert-butyl-4-hydroxyanilino)-s-triazine
N-(3,5-di-tert-butyl-4-hydroxyphenyl)carbamic acid octyl ester.

7. Esters of
β-(3,5-di-tert-butyl-4-hydroxyphenyl)propionic acid with mono- or polyhydric alcohols, e.g. with

| | |
|---|---|
| methanol | diethylene glycol |
| octadecanol | triethylene glycol |
| 1,6-hexanediol | pentaerythritol |
| neopentyl glycol | tris(hydroxyethyl) isocyanurate |
| thiodiethylene glycol | di(hydroxyethyl) oxalic acid diamide |

8. Esters of
β-(5-tert-butyl-4-hydroxy-3-methylphenyl)propionic
acid with mono- or polyhydric alcohols, e.g. with

| | |
|---|---|
| methanol | diethylene glycol |
| octadecanol | triethylene glycol |
| 1,6-hexanediol | pentaerythritol |
| neopentyl glycol | tris(hydroxyethyl) isocyanurate |
| thiodiethylene glycol | di(hydroxyethyl) oxalic acid diamide |

9. Amides of
β-(3,5-di-tert-butyl-4-hydroxyphenyl)propionic acid
e.g.
N,N'-di(3,5-di-tert-butyl-4-hydroxyphenylpropionyl)-hexamethylenediamine
N,N'-di(3,5-di-tert-butyl-4-hydroxyphenylpropionyl)-trimethylenediamine
N,N'-di(3,5-di-tert-butyl-4-hydroxyphenylpropionyl)-hydrazine.

Examples of amine antioxidants:
N,N'-diisopropyl-p-phenylenediamine
N,N'-di-sec-butyl-p-phenylenediamine
N,N'-bis(1,4-dimethylpentyl)-p-phenylenediamine
N,N'-bis(1-ethyl-3-methylpentyl)-p-phenylenediamine
N,N'-bis(1-methylheptyl)-p-phenylenediamine
N,N'-diphenyl-p-phenylenediamine
N,N'-di(naphthyl-2)-p-phenylenediamine
N-isopropyl-N'-phenyl-p-phenylenediamine
N-(1,3,-dimethylbutyl)-N'-phenyl-p-phenylenediamine
N-(1-methylheptyl)-N'-phenyl-p-phenylenediamine
N-cyclohexyl-N'-phenyl-p-phenylenediamine
4-(p-toluenesulfonamido)diphenylamine
N,N'-dimethyl-N,N'-di-sec-butyl-p-phenylenediamine
diphenylamine
4-isopropoxydiphenylamine
N-phenyl-1-naphthylamine
N-phenyl-2-naphthylamine
octylated diphenylamine
4-n-butylaminophenol
4-butyrylaminophenol
4-nonanoylaminophenol
4-dodecanoylaminophenol
4-octadecanoylaminophenol
di(4-methoxyphenyl)amine
2,6-di-tert-butyl-4-dimethylaminomethylphenol
2,4'-diaminodiphenylmethane
4,4'-diaminodiphenylmethane
N,N,N',N'-tetramethyl-4,4'-diaminodiphenylmethane
1,2-di[(2-methylphenyl)amino]ethane
1,2-di(phenylamino)propane
(o-tolyl)biguanide
di[4-(1',3'-dimethylbutyl)phenyl]amine
tert-octylated N-phenyl-1-naphthylamino
mixture of mono- and dialkylated tert-butyl-/tert-octyl-diphenylamines.

Examples of metal passivators are:
for copper, e.g.:
triazole, benzotriazole and their derivates, 2-mercaptobenzothiazole, 2,5-dimercaptothiadiazole, salicylidenepropylenediamine, salts of salicylaminoguanidine.

Examples of rust inhibitors are:
(a) organic acids, their esters, metal salts and anhydrides, e.g.:
N-oleoyl sarcosine, sorbitan mono-oleate, lead naphthenate, dodecenylsuccinic anhydride, alkenylsuccinic acid half esters, 4-nonylphenoxyacetic acid;
(b) nitrogen-containing compounds, e.g.:
(I) primary, secondary or tertiary aliphatic or cycloaliphatic amines and amine salts of organic and inorganic acids, e.g. oil-soluble alkylammoninum carboxylates; and
(II) heterocyclic compounds, e.g.: substituted imidazolines and oxazolines.
(c) phosphorus-containing compounds, e.g.: amine salts of phosphoric acid partial esters
(d) sulfur-containing compounds, e.g.: barium dinonyl naphthalene sulfonates and calcium petroleum sulfonates.

Examples of viscosity-index improvers are:
polymethacrylates, vinylpyrrolidone/methacrylate copolymers, polybutenes, olefin copolymers, styrene/acrylate copolymers.

Examples of pour-point depressants are:
polymethacrylates and alkylated naphthalene derivatives.

Examples of dispersing agents/surfactants are:
polybutenylsuccinic acid imides, polybutenylphosphonic acid derivatives, and basic Mg, Ca and Ba sulfonates and Mg, Ca and Ba phenolates.

Examples of anti-wear additives are:
compounds containing sulfur and/or phosphorus and/or halogen, e.g.: sulfurised vegetable oils, zinc dialkyl dithiophosphates, tritolyl phosphate, chlorinated paraffins, alkyl disulfides and aryl disulfides.

The compounds of formula I are useful as additives in particular to lubricating systems, especially engine oils, in which they exhibit corrosion-inhibiting properties. Relative to known compounds having comparable properties, the compounds of formula I are advantageous in that they are phosphorus- and tin-free so that not even the after-combustion of the exhaust gases is impaired.

EXAMPLE 1

10.5 parts of diethanolamine are added dropwise on to 22.8 parts of tert-nonylcarboxyglycidyl ether at 60° C. and the resultant solution is stirred for 3 hours. The crude product is distilled to give 28.1 parts of N,N-di(-hydroxyethyl)-2-hydroxy-3-tert-nonylcarbonyloxypropylamine. Boiling point: 225° C./0.13 mb.

EXAMPLE 2

10.5 parts of diethanolamine are heated to 60° C. and 27.1 parts of tert-dodecylglycidyl thioether are added dropwise. After completion of the addition, the mixture is stirred for 1 hour at 70° C. 3-tert-Dodecylthio-1-[di(2-hydroxyethyl)amino]propan-2-ol is obtained as a yellow viscous liquid having refractive index $n_D^{20} = 1.4972$ in a yield of 100% of theory.

EXAMPLE 3

By following a procedure analogous to that of Example 2, 21 parts of diethanolamine are reacted with 45.4 parts of tertnonylglycidyl thioether to produce 3-tert-nonylthio-1-[di(2-hydroxyethyl)amino]propan-2-ol as a yellow viscous liquid having refractive index $n_D^{20} = 1.5008$ in a yield of 100% of theory.

EXAMPLES 4 TO 21

Further compounds of formula I

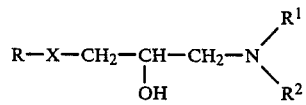

are prepared by following a procedure analogous to those of Examples 1 and 2. These compounds are listed in Table 2.

TABLE 2

| Ex. | R | X | $R^1$ | $R^2$ | b.p. (°C.)/mb |
|---|---|---|---|---|---|
| 4  | $t$-$C_9H_{19}$ | —CO—O— | $(CH_2)_3OH$ | $(CH_2)_3OH$ | viscous oil |
| 5  | $t$-$C_9H_{19}$ | —CO—O— | $CH_3$ | $CH_2CH_2OH$ | 200/0.065 |
| 6  | $t$-$C_9H_{19}$ | —CO—O— | $CH_2CHOHCH_3$ | $CH_2CHOHCH_3$ | 200/0.05 |
| 7  | $i$-$C_8H_{17}$ | —O— | $CH_2CH_2OH$ | $CH_2CH_2OH$ | 190/2.34 |
| 8  | $i$-$C_8H_{17}$ | —O— | $(CH_2)_3OH$ | $(CH_2)_3OH$ | viscous oil |
| 9  | $i$-$C_8H_{17}$ | —O— | $CH_3$ | $CH_2CH_2OH$ | 180/0.065 |
| 10 | $i$-$C_8H_{17}$ | —O— | $CH_2CHOHCH_3$ | $CH_2CHOHCH_3$ | 180/0.05 |
| 11 | $CH_2$=$CHCH_2$ | —O— | $CH_2CH_2OH$ | $CH_2CH_2OH$ | 210/0.05 |
| 12 | $C_4H_9CH(C_2H_5)CH_2$ | —$N(CH_2CH(C_4H_9)C_2H_5)$— | $CH_2CH_2OH$ | $CH_2CH_2OH$ | viscous oil |
| 13 | $C_4H_9CH(C_2H_5)CH_2$ | —$N(CH_2CH(C_4H_9)C_2H_5)$— | $(CH_2)_3OH$ | $(CH_2)_3OH$ | viscous oil |
| 14 | $\begin{array}{c}OH\quad CH_2CH_2OH\\ |\quad /\\ CH_2CHCH_2N\\ \quad\backslash\\ \quad CH_2CH_2OH\end{array}$ | —$N(C_{12}H_{25})$— | $CH_2CH_2OH$ | $CH_2CH_2OH$ | 170/0.35 |
| 15 | $t$-$C_9H_{19}$ | —S— | $CH_2CH_2OH$ | H | |
| 16 | $t$-$C_9H_{19}$ | —S— | $CH_3$ | $CH_2CH_2OH$ | |
| 17 | $t$-$C_{12}H_{25}$ | —S— | $CH_2CH_2OH$ | $CH_2CH_2OH$ | 155/0.16 |
| 18 | $t$-$C_9H_{19}$ | —S— | $CH_2CH_2OH$ | $CH_2CH_2OH$ | |
| 19 | $t$-$C_{16}H_{33}$ | —S— | $CH_2CH_2OH$ | $CH_2CH_2OH$ | viscous oil |
| 20 | $t$-$C_9H_{19}$ | —S— | $C(CH_2OH)_3$ | H | m.p. 61–63° C. |
| 21 | $t$-$C_{12}H_{25}$ | —S— | $C(CH_2OH)_2C_2H_5$ | H | viscous oil |
| 22 | $t$-$C_{16}H_{33}$ | —S— | $C(CH_2OH)_3$ | H | viscous oil |
| 23 | $t$-$C_4H_9$ | —S— | $C(CH_2OH)_3$ | H | |
| 24 | $C_2H_5$ | —S— | $C(CH_2OH)_3$ | H | |

EXAMPLES 22 TO 28

Several products of Examples 1 to 21 are tested as rust inhibitors in a turbine grade mineral oil of viscosity 26 mm²/g at 40° C., 4.8 mm²/g at 100° C. and a typical sulphur content of 0.6%, using the ASTM D665A (deionised water) and D665B (synthetic sea water) methods. The results are set out in Table 3 and are expressed as the concentration (ppm) of the product which will prevent any trace of rusting of the test spindle. In both A and B tests, the absence of additive causes severe rusting of the test spindle to occur.

TABLE 3

| | | Minimum concentration for zero rust | |
|---|---|---|---|
| Example | Test compound | A test ppm | B test ppm |
| 22 | Product of Ex. 1 | <250 | <250 |
| 23 | Product of Ex. 4 | | <500 |
| 24 | Product of Ex. 7 | <125 | <125 |
| 25 | Product of Ex. 8 | | <500 |
| 26 | Product of Ex. 2 | | <500 |
| 27 | Product of Ex. 3 | <125 | <125 |
| 28 | Product of Ex. 15 | <250 | <500 |

What is claimed is:

1. A composition having corrosion inhibiting properties which comprises a non-aqueous functional liquid and an effective corrosion-inhibiting amount of at least one compound of formula I

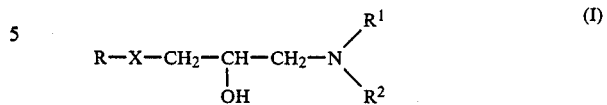

wherein X is —O— $R^1$ is unsubstituted $C_1$–$C_4$alkyl or $C_2$–$C_5$alkyl substituted by one to three hydroxyl groups, $R^2$ is hydrogen, unsubstituted $C_1$ $C_4$alkyl or $C_2$–$C_5$alkyl substituted by one to three hydroxyl groups, with the proviso that at least one of the residues $R^1$ or $R^2$ is hydroxy-substituted, and R is branched $C_4$–$C_{20}$alkyl, $C_2$–$C_{18}$alkenyl, $C_2$–$C_3$alkynyl or $C_5$–$C_{12}$cycloalkyl.

2. A composition according to claim 1, wherein in formula I R is tertiary $C_4$–$C_{20}$alkyl.

3. A composition according to claim 1, wherein in formula I $R^1$ and $R^2$ are $C_2$–$C_5$alkyl monosubstituted by hydroxy.

4. A composition according to claim 1, wherein the non-aqueous functional fluid is a lubricating oil, a refined petroleum product or a hydraulic fluid.

5. A composition according to claim 4, wherein the lubricating oil is a mineral oil.

6. A composition according to claim 4, wherein the hydraulic fluid is a synthetic oil.

7. A composition according to claim 1, wherein the amount of compound of formula I is 0.001 to 5% by weight, based on the non-aqueous functional fluid.

8. A composition according to claim 4, wherein the functional fluid contains further additives selected from the group consisting of antioxidants, metal passivators, rust inhibitors, viscosity-index improvers, pour-point depressants, dispersing agents, emulsifiers, extreme pressure additives and anti-wear additives.

* * * * *